US010507310B2

United States Patent
Matlock et al.

(10) Patent No.: US 10,507,310 B2
(45) Date of Patent: Dec. 17, 2019

(54) DILATION APPARATUS WITH MALLEABLE FEATURE AND APPARATUS TO BEND MALLEABLE FEATURE

(71) Applicant: Acclarent, Inc., Irvine, CA (US)

(72) Inventors: George L. Matlock, Pleasanton, CA (US); Jason R. Phillips, Rancho Santa Margarita, CA (US)

(73) Assignee: Acclarent, Inc., Irvine, CA (US)

( * ) Notice: Subject to any disclaimer, the term of this patent is extended or adjusted under 35 U.S.C. 154(b) by 489 days.

(21) Appl. No.: 15/335,806

(22) Filed: Oct. 27, 2016

(65) Prior Publication Data

US 2018/0117290 A1  May 3, 2018

(51) Int. Cl.
| | |
|---|---|
| *B21D 7/022* | (2006.01) |
| *A61M 29/02* | (2006.01) |
| *A61B 17/24* | (2006.01) |
| *B21D 7/06* | (2006.01) |
| *B21C 37/08* | (2006.01) |
| *B21D 7/04* | (2006.01) |
| *B21D 7/03* | (2006.01) |
| *A61B 17/00* | (2006.01) |
| *A61M 25/01* | (2006.01) |

(52) U.S. Cl.
CPC .............. *A61M 29/02* (2013.01); *A61B 17/24* (2013.01); *A61B 2017/00946* (2013.01); *A61B 2017/246* (2013.01); *A61M 25/0136* (2013.01); *A61M 2210/0681* (2013.01); *B21C 37/0815* (2013.01); *B21D 7/03* (2013.01); *B21D 7/04* (2013.01); *B21D 7/06* (2013.01); *B21D 7/063* (2013.01); *B21D 7/066* (2013.01)

(58) Field of Classification Search
CPC .......... B21D 7/063; B21D 7/04; B21D 7/066; B21D 7/06; B21D 7/03; B21C 37/0815; A61M 29/02; A61M 25/0136; A61M 2210/0681; A61B 2017/00946; A61B 2017/246; A61B 17/24
USPC ........................................................... 72/457
See application file for complete search history.

(56) References Cited

U.S. PATENT DOCUMENTS

| | | | |
|---|---|---|---|
| 4,005,593 A | | 2/1977 | Goldberg |
| 4,206,629 A | * | 6/1980 | Grimaldo ................. B21D 7/06 72/389.1 |
| 4,641,516 A | | 2/1987 | Satoh |
| 5,125,252 A | | 6/1992 | Ayres et al. |
| 5,761,950 A | * | 6/1998 | Chiu ....................... B21D 7/063 72/389.1 |

(Continued)

FOREIGN PATENT DOCUMENTS

EP   2 810 611 A1   12/2014

OTHER PUBLICATIONS

International Search Report and Written Opinion dated Jan. 15, 2018 for Application No. PCT/US2017/057988, 11 pgs.

*Primary Examiner* — David B Jones
(74) *Attorney, Agent, or Firm* — Frost Brown Todd LLC

(57) ABSTRACT

An apparatus includes a guide member configured with stress limiting features which function to prevent the stress from bending the guide member causing ovalization of the guide member. An apparatus for bending a guide member includes a ram die and a pressure die which are configured to fully encircle the portion of the guide member during the bending operation. A fixture for supporting a guide member during bending is configured to fully encircle sections of the guide member during bending.

20 Claims, 15 Drawing Sheets

(56) References Cited

U.S. PATENT DOCUMENTS

| | | | |
|---|---|---|---|
| 6,523,388 B1 * | 2/2003 | Winton, III | B21D 7/066 |
| | | | 72/389.1 |
| 7,462,175 B2 | 12/2008 | Chang et al. | |
| 7,624,612 B2 * | 12/2009 | Toda | B21D 7/04 |
| | | | 72/389.1 |
| 7,669,448 B1 * | 3/2010 | Gharib | B21C 37/0815 |
| | | | 72/51 |
| 9,144,835 B2 * | 9/2015 | Houle | B21D 7/063 |
| 9,155,492 B2 | 10/2015 | Jenkins et al. | |
| 9,700,326 B2 | 7/2017 | Morriss et al. | |
| 2010/0030031 A1 | 2/2010 | Goldfarb et al. | |
| 2011/0004057 A1 | 1/2011 | Goldfarb et al. | |
| 2012/0071857 A1 | 3/2012 | Goldfarb et al. | |
| 2014/0074141 A1 | 3/2014 | Johnson et al. | |

* cited by examiner

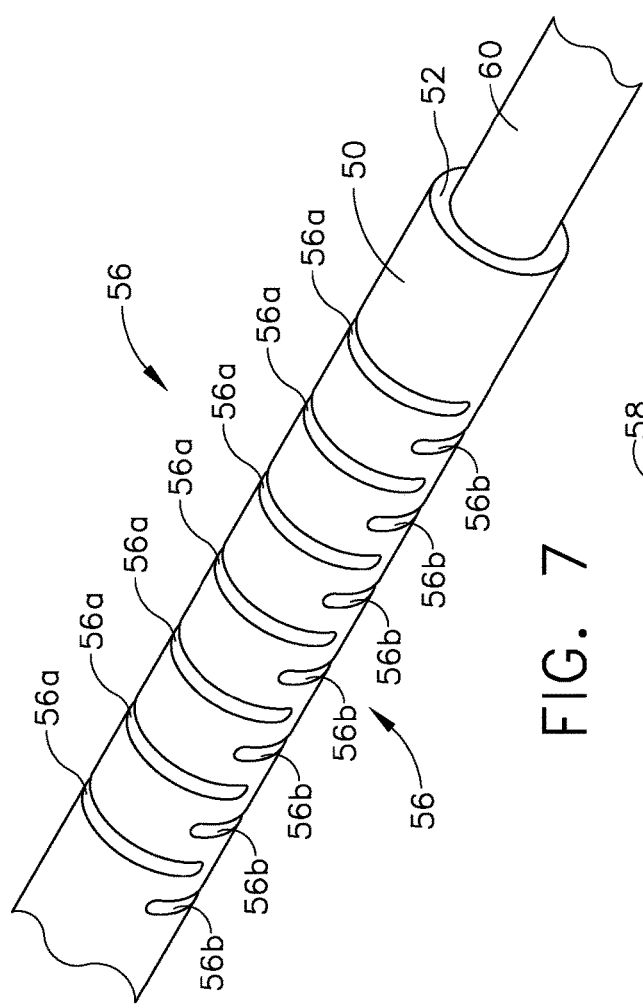
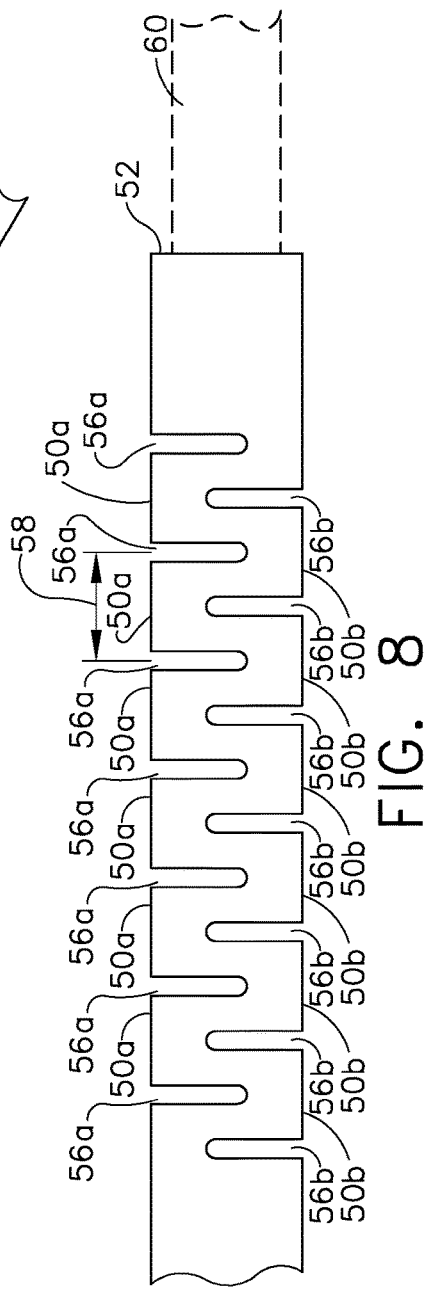

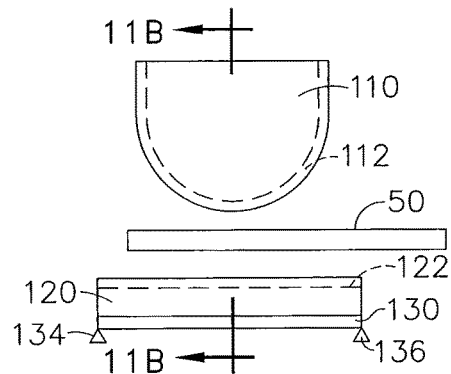 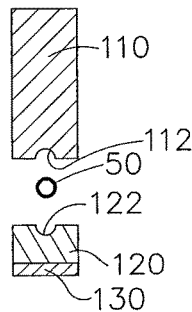
FIG. 11A  FIG.11B
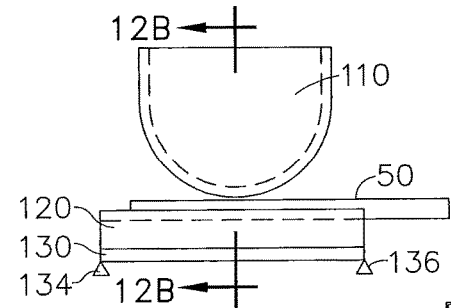 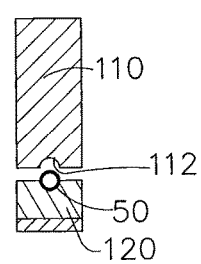
FIG. 12A  FIG. 12B
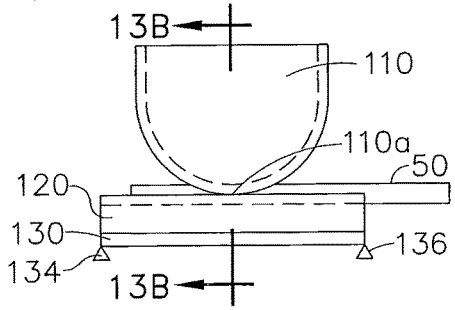 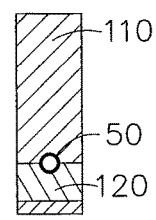 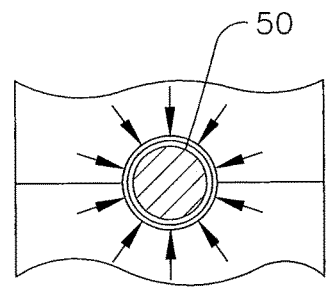
FIG. 13A  FIG. 13B  FIG. 13C
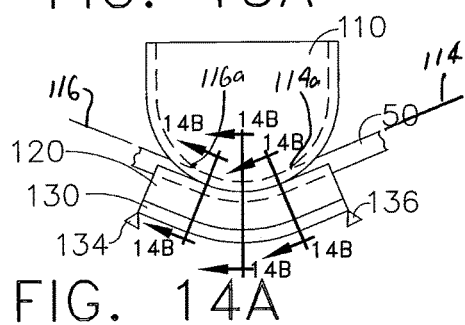 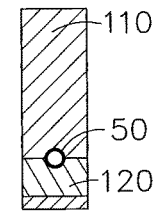
FIG. 14A  FIG. 14B

DILATION APPARATUS WITH MALLEABLE FEATURE AND APPARATUS TO BEND MALLEABLE FEATURE

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It often is desirable to alter the angle of the distal end of a guide member in order to access an anatomical passageway. As a result of the bending process to alter the angle, a change in cross-sectional shape may occur in which internal and/or external dimensions may change and thereby increase resistance to the movement of internal components through or of external components about the guide member. While several systems and methods have been made to avoid such problems, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7 depicts a perspective view of an exemplary alternative malleable guide member with stress limiting features;

FIG. 8 depicts a side view of the malleable guide member of FIG. 7 with the guidewire omitted from inside of the malleable guide member;

FIG. 11A depicts a side view of the bending instrument and malleable guide member of FIG. 10, with the bending instrument in an open configuration;

FIG. 11B depicts a cross-sectional view of the bending instrument and malleable guide member of FIG. 10, taken along 11B-11B of FIG. 11A;

FIG. 12A depicts a side view of the bending instrument and malleable guide member of FIG. 10, with the bending instrument in a partially closed configuration;

FIG. 12B depicts a cross-sectional view of the bending instrument and malleable guide member of FIG. 10, taken along 12B-12B of FIG. 12A;

FIG. 13A depicts a side view of the exemplary bending instrument and malleable guide member of FIG. 10, with the bending instrument in a closed configuration;

FIG. 13B depicts a cross-sectional view of the bending instrument and malleable guide member of FIG. 10, taken along 13B-13B of FIG. 13A;

FIG. 13C depicts a partial cross-sectional view of the bending instrument and malleable guide member of FIG. 10, taken along 13B-13B of FIG. 13A, showing a schematic representation of forces exerted by the bending instrument on the malleable guide member;

FIG. 14A depicts a side view of the exemplary bending instrument and malleable guide member of FIG. 10, with the bending instrument in a closed configuration and the malleable guide member in a partially bent configuration;

FIG. 14B depicts a cross-sectional view of the bending instrument and malleable guide member of FIG. 10, taken along 14B-14B of FIG. 14A;

Figure 1A:
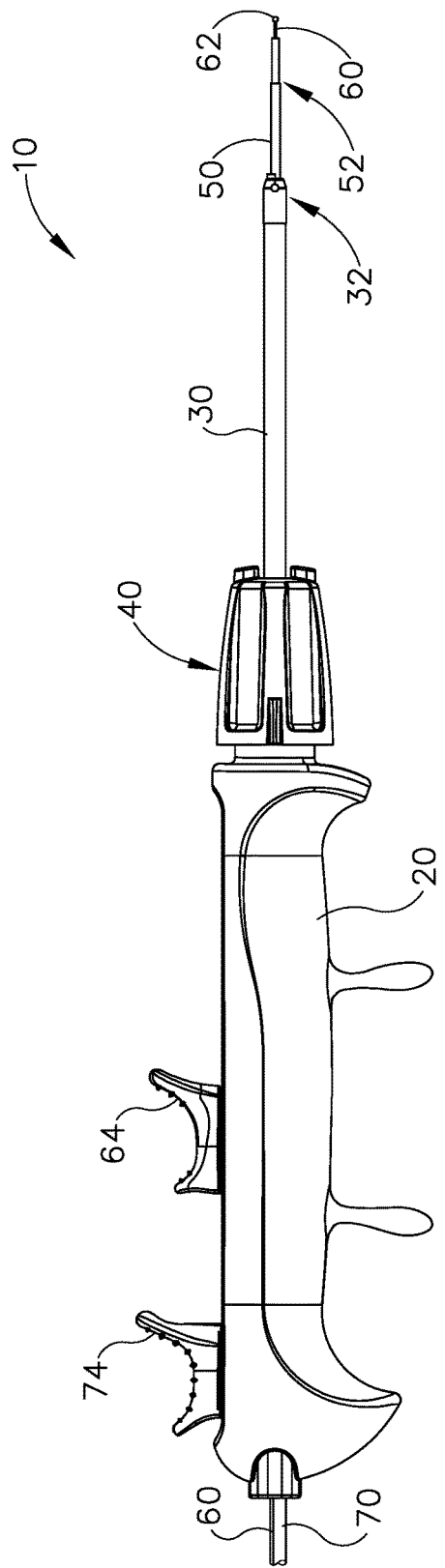
FIG. 1A depicts a side elevational view of an exemplary dilation instrument, in an initial configuration.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

Figure 1B:
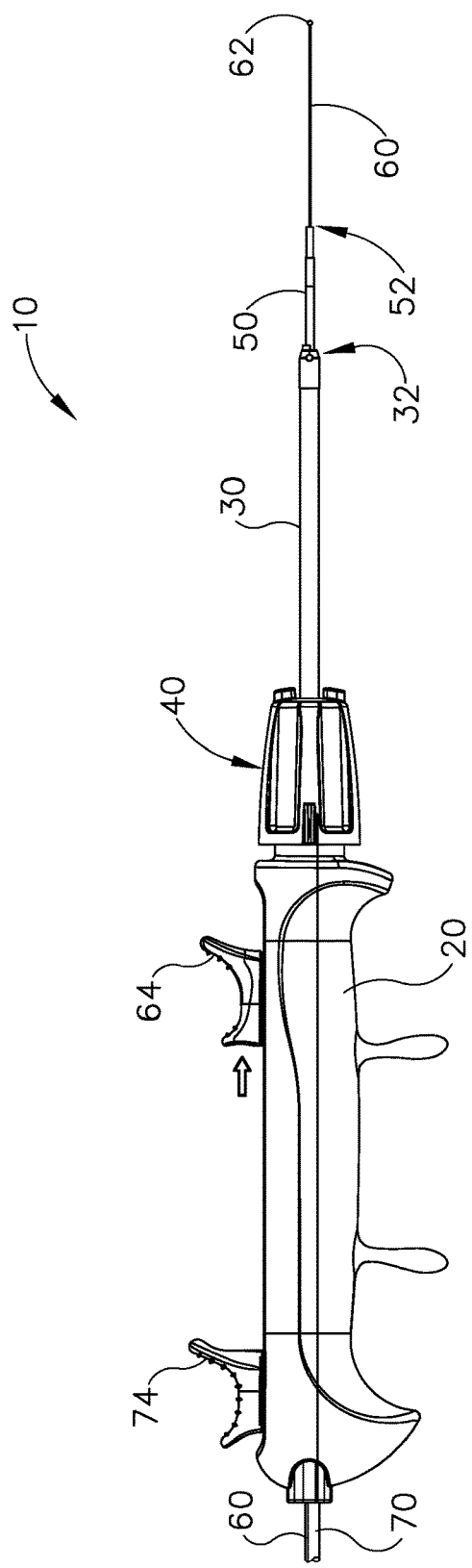
FIG. 1B depicts a side elevational view of the dilation instrument of FIG. 1A, with a guidewire advanced to a distal position.
Figure 1C:
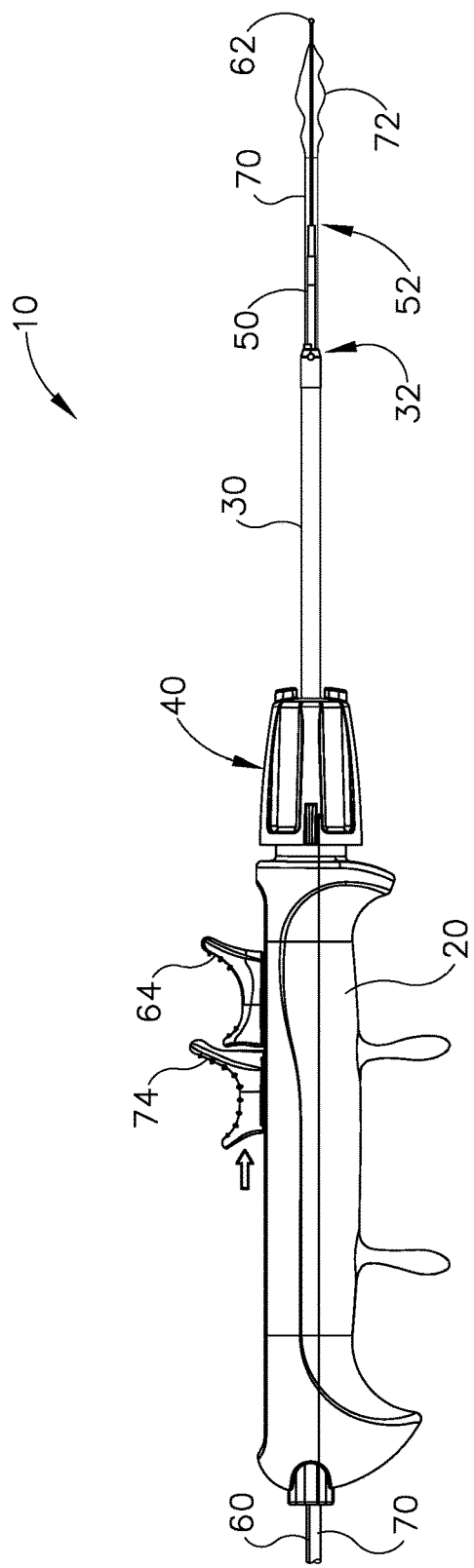
FIG. 1C depicts a side elevational view of the dilation instrument of FIG. 1A, with a dilation catheter advanced to a distal position.

FIGS. 1A-1C show an exemplary dilation instrument (10) that may be used to dilate the ostium of a paranasal sinus; or to dilate some other anatomical passageway (e.g., within the ear, nose, or throat, etc.). By way of example only, dilation instrument (10) may be configured and operable in accordance with at least some of the teachings of U.S. Pub. No. 2012/0071857, entitled "Methods and Apparatus for Treating Disorders of the Sinuses," published Mar. 22, 2012, now abandoned, the disclosure of which is incorporated by reference herein. In addition or in the alternative, dilation instrument (10) may be configured and operable like the Relieva Scout® Sinus Dilation System by Acclarent, Inc. of Menlo Park, Calif.

Dilation catheter system (10) of the present example comprises a handle assembly (20), a rigid guide member (30), a rotary knob (40), a malleable guide member (50), a guidewire (60), and a dilation catheter (70). Handle assembly (20) is configured to be gripped by a single hand of an operator. Rigid guide member (30) extends distally from handle assembly (20) and is substantially straight. In some versions, rigid guide member (30) is formed of metal, though any other suitable material(s) may be used. In the present example, the longitudinal position and angular position of rigid guide member (30) is fixed relative to handle assembly (20).

Malleable guide member (50) protrudes distally from the open distal end (32) of rigid guide member (30). The outer diameter of malleable guide member (50) is smaller than the inner diameter of rigid guide member (30), such that a cylindraceous gap is defined between the outer diameter of malleable guide member (50) and the inner diameter of rigid guide member (30). This cylindraceous gap is sized to accommodate a translating dilation catheter (70) as will be described in greater detail below. While malleable guide member (50) is shown as having a straight configuration in FIGS. 1A-1C, malleable guide member (50) may be bent to various bend angles as shown in FIGS. 2A, and 3-5; and as will be described in greater detail below. Malleable guide member (50) is configured to substantially maintain a bend angle once bent, until the operator takes steps to intentionally unbend or re-bend malleable guide member (50). In other words, malleable guide member (50) has sufficient rigidity to maintain a selected bend angle during operation of dilation instrument (10) in a dilation procedure, such that use of dilation instrument (10) in a dilation procedure will not cause malleable guide member (50) to undesirably unbend or re-bend. In the present example, malleable guide member (50) is formed of metal, though any other suitable material(s) may be used. While the term "malleable" is used to describe guide member (50), that term should not be read as requiring guide member (50) to have undergone an annealing process or any other process to increase the ductility of steel. In some instances, rigid guide member (30) and malleable guide member (50) are formed of the exact same material (e.g., full hard stainless steel), yet the differences in size and thickness provide greater rigidity in guide member (30) than in guide member (50).

Guidewire (60) is slidably received in a central lumen (54) defined in malleable guide member (50). Guidewire (60) includes a rounded tip feature (62) that is located distal to the open distal end (52) of malleable guide member (50). Guidewire (60) is secured to a slider (64), which is slidably coupled with handle assembly (20). Slider (64) is thus operable to slide guidewire (60) between a proximal position (FIG. 1A) and a distal position (FIG. 1B). In the present example, tip feature (62) has an outer diameter that is larger than the inner diameter of distal end (52) of malleable guide member (50), such that tip feature (62) cannot be retracted proximally back through malleable guide member (50). In some versions, guidewire (60) includes one or more optical fibers, and tip feature (62) is configured to emit light communicated through such optical fibers. This may enable an operator to verify positioning of tip feature (62) within a sinus cavity through a transillumination effect as is known in the art. The proximal end of guidewire (60) may be coupled with a suitable light source. By way of example only, guidewire (60) may be configured and operable in accordance with at least some of the teachings of U.S. Pub. No. 2012/0078118, issued as U.S. Pat. No. 9,155,492 on Oct. 13, 2015, the disclosure of which is incorporated by reference herein. In addition or in the alternative, guidewire (60) may be configured and operable like the Relieva Luma Sentry® Sinus Illumination System by Acclarent, Inc. of Menlo Park, Calif. Other suitable forms that guidewire (60) may take will be apparent to those of ordinary skill in the art in view of the teachings herein.

Figure 2A:
FIG. 2A depicts a side elevational view of the distal end of the dilation instrument of FIG. 1A, with the guidewire advanced to the distal position.
Figure 2B:
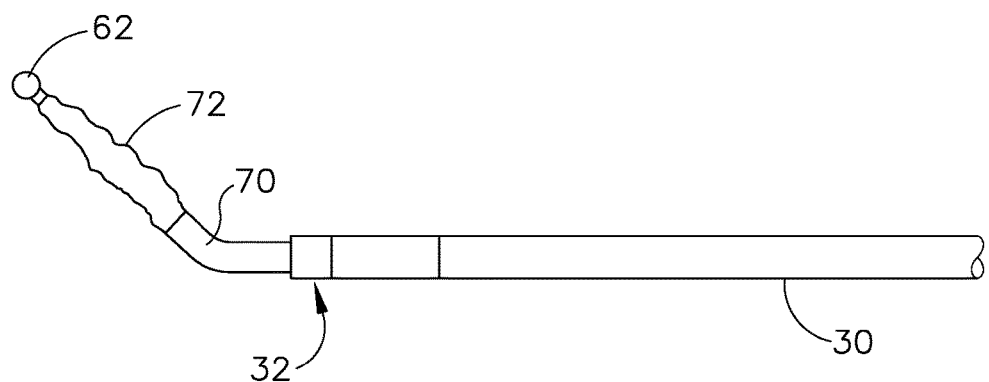
FIG. 2B depicts a side elevational view of the distal end of the dilation instrument of FIG. 1A, with a dilation catheter advanced to a distal position.

Dilation catheter (70) is sildably disposed along malleable guide member (50) and is thus operable to translate through the cylindraceous gap is defined between the outer diameter of malleable guide member (50) and the inner diameter of rigid guide member (30). Dilation catheter (70) is secured to a slider (74), which is slidably coupled with handle assembly (20). Slider (74) is thus operable to slide dilation catheter (70) between a proximal position (FIGS. 1B and 2A) and a distal position (FIGS. 1C and 2B). When dilation catheter (70) translates from the proximal position to the distal position dilation catheter (70) passes over the open distal end (52) of malleable guide member (50) and then traverses along at least a portion of the length of guidewire (60) that extends distally from open distal end (52) of malleable guide member (50). In some versions, dilation instrument (10) is configured such that dilation catheter (70) is unable to translate distally to a position where the distal end of dilation catheter (70) is distal to tip feature (62) of guidewire (60). For instance, slider (74) may engage slider (64) when dilation catheter (70) is driven to a distal-most position, and this engagement between sliders (64, 74) may prevent the distal end of dilation catheter (70) from engaging or otherwise passing distally over tip feature (62) of guidewire (60). This engagement may also enable slider (74) to be used to advance a proximally positioned guidewire (60) and dilation catheter (70) distally simultaneously, since slider (74) would drive a proximally positioned slider (64) distally. Thus, instrument (10) need not necessarily be operated in a manner where guidewire (60) is advanced distally, as a discrete act in a sequence, before dilation catheter (70) is advanced distally.

Figure 2C:
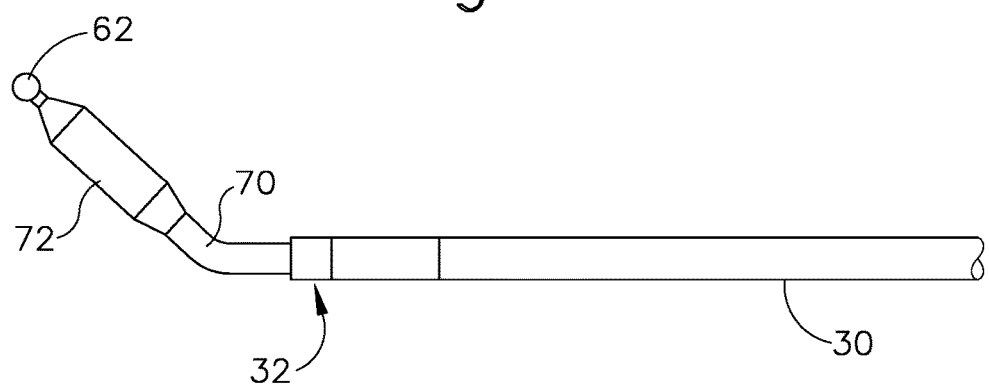
FIG. 2C depicts a side elevational view of the distal end of the dilation instrument of FIG. 1A, with a dilator of the dilation catheter in an expanded state.

The distal end of dilation catheter (70) comprises a dilator (72). Dilator (72) is operable to transition between a non-expanded state (FIG. 2B) and an expanded state (FIG. 2C). In the non-expanded state, dilator (72) may be inserted into a sinus ostium or other drainage passageway associated with a paranasal sinus. Dilator (72) may then be expanded to dilate the sinus ostium or other drainage passageway as described in various references herein. In the present example, dilator (72) comprises an inflatable balloon that receives saline (or some other fluid) for inflation, though it should be understood that dilator (72) may instead take a variety of other forms. In some versions, dilation catheter (70) is fluidly coupled with an inflator instrument that is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

Figure 3:
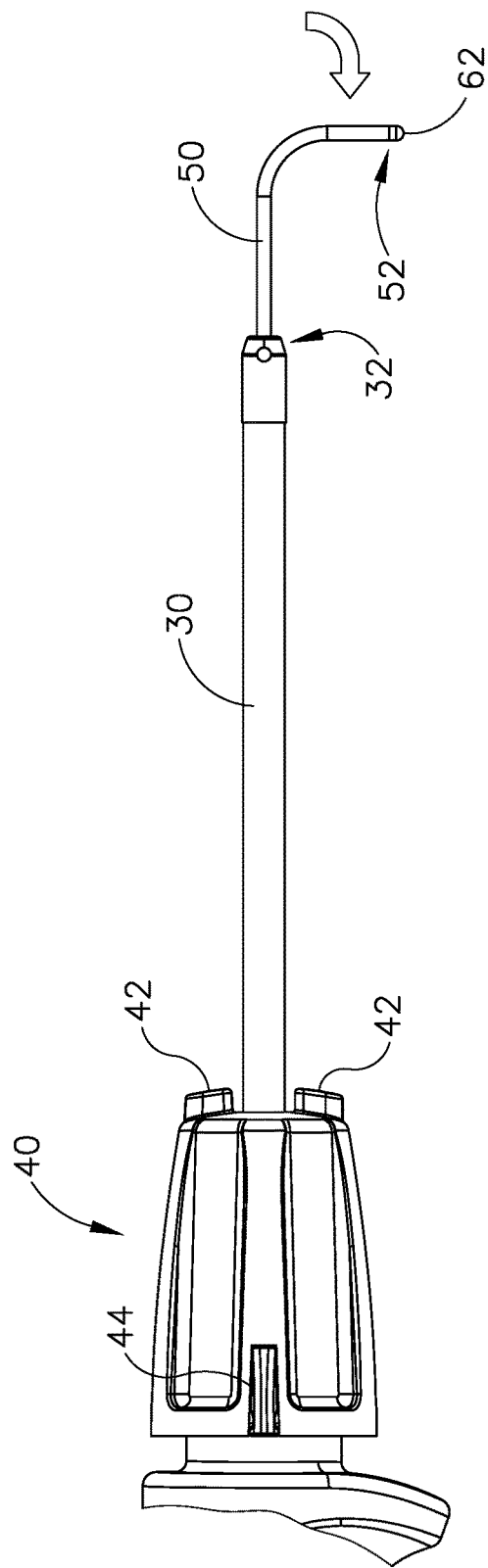
FIG. 3 depicts a side elevational view of a shaft assembly of the dilation instrument of FIG. 1A, with a malleable guide member bent downwardly.
Figure 4:
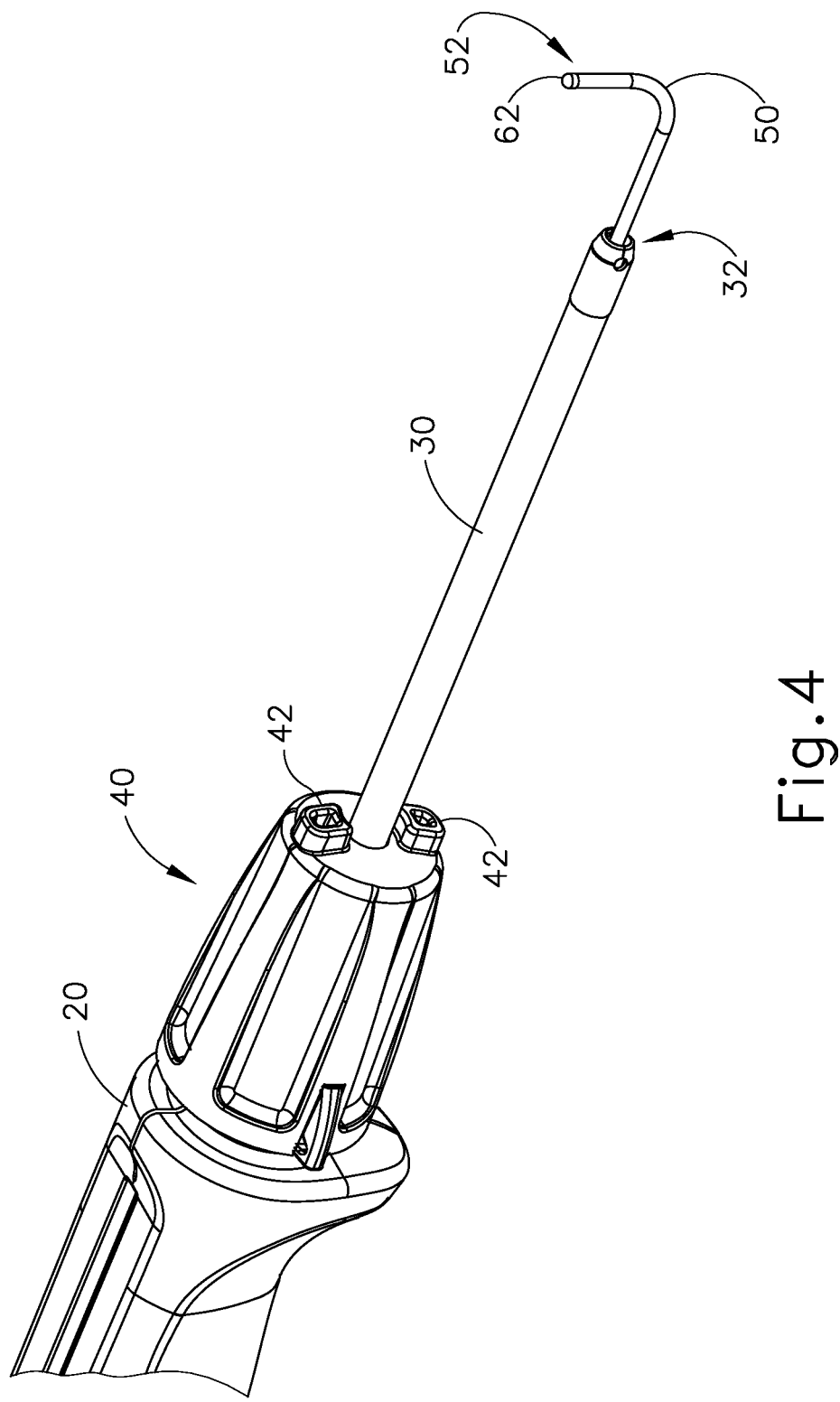
FIG. 4 depicts a perspective view of the shaft assembly of FIG. 3, with the malleable guide member bent upwardly.
Figure 5:
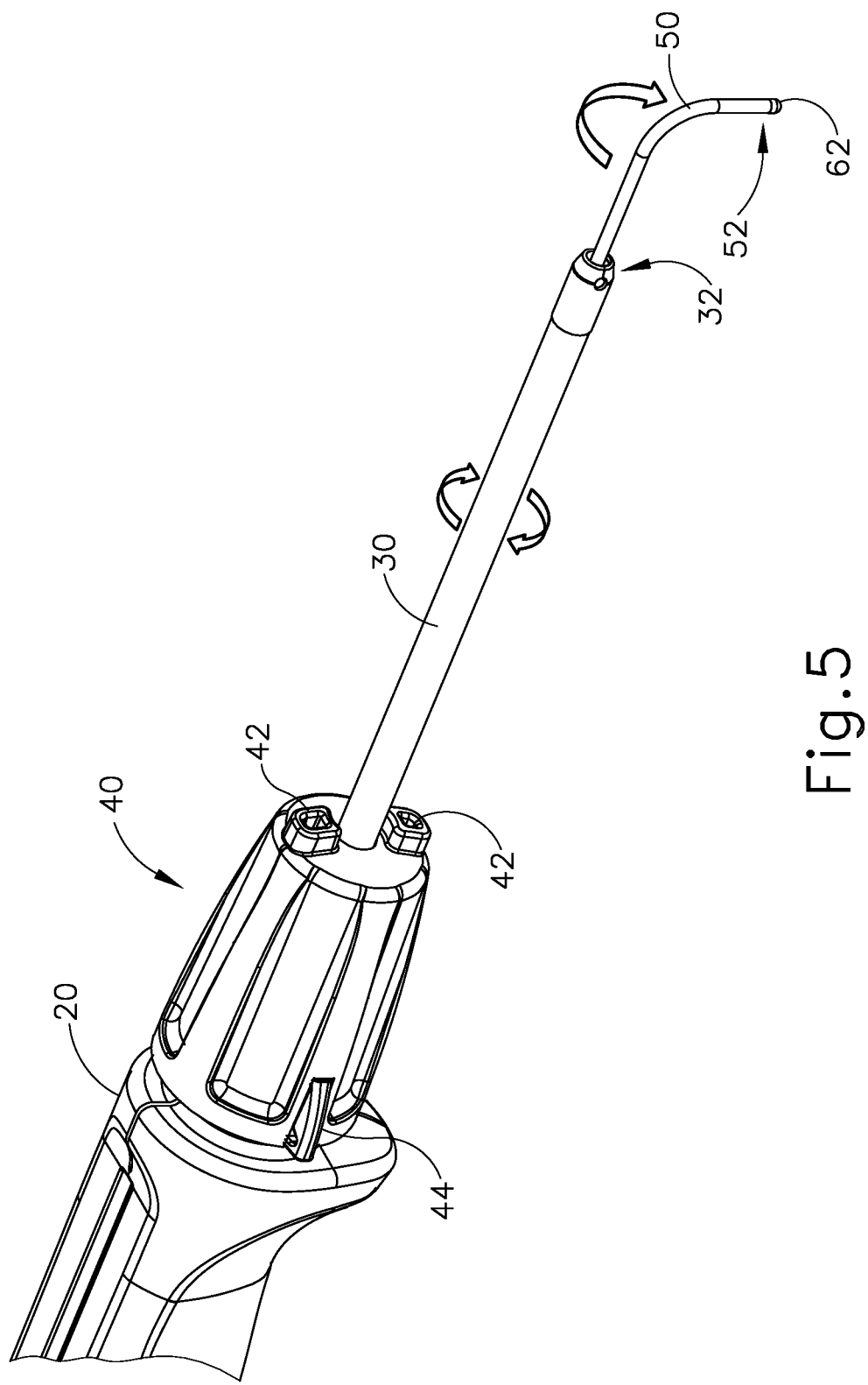
FIG. 5 depicts a perspective view of the shaft assembly of FIG. 3, with the shaft assembly rotated to re-orient the malleable guide member downwardly.

Rotary knob (40) is fixedly secured to the proximal end of malleable guide member (50). As shown in FIGS. 3 and 5, rotary knob (40) includes a pair of distally projecting bosses (42) and a laterally projecting indicator fin (44). Bosses (42) are angularly spaced from each other by 180° about the longitudinal axis of rigid guide member (30). Rotary knob (40) is configured to rotate and translate about rigid guide member (30), though the degree of rotation and the degree of translation are limited. In particular, as shown in FIGS. 4-5, rotary knob (40) is configured to rotate through an angular range of 180° about the longitudinal axis of rigid guide member (30). In the present example, this angular range provides rotation of rotary knob (40) between a position where indicator fin (44) is located at the 3 o'clock angular position (i.e., pointing to the right when viewing instrument (10) from the distal end toward the proximal end, as shown in FIG. 4) and a position where indicator fin (44) is located at the 9 o'clock angular position (i.e., pointing to the right when viewing instrument (10) from the distal end toward the proximal end, as shown in FIGS. 1A-1C, 3, 5-7B, and 17-18). In the present example, an operator would rotate rotary knob (40) based on whether the operator is grasping instrument (10) with their left hand or right hand, as will be described in greater detail below.

As also shown in FIGS. 4-5, rotation of rotary knob (40) also rotates malleable guide member (50), thereby re-orienting distal end (52) of malleable guide member (50) and tip feature (62) of guidewire (60). An operator may wish to provide such rotation and re-orientation based on the sinus in which guidewire (60) and dilation catheter (70) are to be inserted. In addition or in the alternative, an operator may wish to provide such rotation and re-orientation in order to facilitate right-handed use or left-handed use of dilation instrument (10).

In the present example, the angular position of rotary knob (40) and malleable guide member (50) is selectively locked or unlocked based on longitudinal positioning of rotary knob (40) relative to handle assembly (20). In particular, when rotary knob (40) is in a distal longitudinal position, the angular position of rotary knob (40) and malleable guide member (50) is locked. When rotary knob

(40) is in a proximal longitudinal position, the angular position of rotary knob (40) and malleable guide member (50) is unlocked. A resilient member biases rotary knob (40) to the distal position. Thus, in order to rotate rotary knob (40) and malleable guide member (50) about the longitudinal axis of rigid guide member (30), the operator may grasp rotary knob (40), pull rotary knob (40) proximally, rotate rotary knob (40) to achieve a desired angular position while still pulling rotary knob (40) proximally, then release rotary knob (40) to allow rotary knob (40) to return to the distal position. Various suitable structural features that may be incorporated into instrument to provide this functionality will be apparent to those of ordinary skill in the art in view of the teachings herein. Also, in the present example, rotary knob (40) provides three discrete angular locking positions (e.g., 12 o'clock, 3 o'clock, and 9 o'clock). However, some other versions may provide additional discrete angular locking positions.

In some instances, dilation instrument (10) is used in combination with an endoscope, which provides visualization in the sinus cavity of the patient. The operator may thus position dilation instrument (10) at the appropriate sinus ostium, other outflow tract, etc., under visual guidance from the endoscope. By way of example only, such an endoscope may be configured and operable in accordance with at least some of the teachings of U.S. Pub. No. 2010/0030031, now abandoned, the disclosure of which is incorporated by reference herein. In addition or in the alternative, such an endoscope may be configured and operable like the Acclarent Cyclops™ Multi-Angle Endoscope by Acclarent, Inc. of Menlo Park, Calif. Of course, any other suitable kind of device(s) may be used to provide visualization during use of dilation instrument (10).

II. Exemplary Malleable Guide Member

Figure 6A:
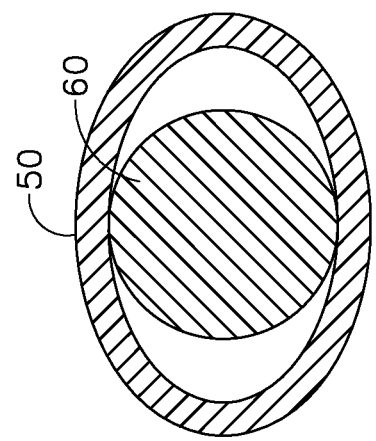
FIG. 6A depicts an initial cross-sectional shape of the malleable guide member of FIG. 3.

As seen in the cross-section illustrated in FIG. 6A, guidewire (60) is disposed in central lumen (54). Malleable guide member (50) has a generally internal and external circular cross-sectional shape. The external circular shape helps trackability of dilation catheter (70) and the internal circular shape helps trackability of guidewire (60). The internal shape is configured relative to guidewire (60) to provide internal clearance between malleable guide member (50) and guidewire (60) to minimize resistance to the movement of guidewire (60) between a proximal position (FIG. 1A) and a distal position (FIG. 1B). As indicated above, malleable guide member (50) may be bent to a desired angle or angles, and the selected angle or angles will be maintained by malleable guide member (50) until the operator takes steps to intentionally unbend or re-bend malleable guide member (50).

It is desirable to maintain the internal and external shape of malleable guide member (50), to maintain the internal clearance between malleable guide member (50) and guidewire (60), and to maintain the external shape of malleable guide member (50) throughout the bending procedure. A change in the external shape of malleable guide member (50) can adversely affect the trackability of dilation catheter (70) over malleable guide member (50) and a reduction in the internal clearance in any direction can increase the resistance to movement of guidewire (60) within malleable guide member (50).

Figure 6B:
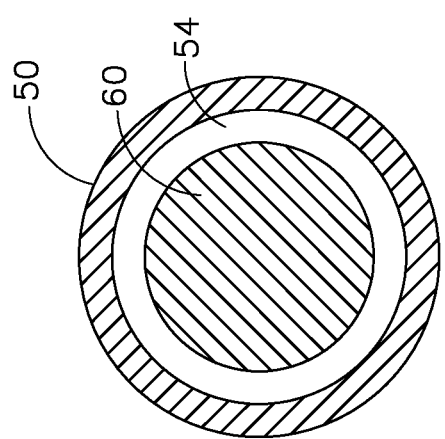
FIG. 6B depicts an ovalized cross-sectional shape of the malleable guide member of FIG. 3.

During the bending process, the internal and external shape of malleable guide member (50) can change from its initial generally circular cross-sectional shape. FIG. 6B illustrates a change in the initial dimensions (see FIG. 6A), passing through a centrally located internal point, between corresponding opposed points on opposite surfaces. In the exemplary malleable guide member (50) illustrated in FIGS. 6A & 6B, the initial shape shown in FIG. 6A is circular, and the bending process has caused ovalization as shown in FIG. 6B. The vertical diameter has reduced and the horizontal diameter has increased resulting in a generally oval shape. Ovalization, as used herein, means that one or more initial internal or external dimensions between corresponding opposed points have decreased and that one or more initial internal or external dimensions between corresponding opposed points have increased.

The change from initial shape due to bending, such as with ovalization, may occur when the stress on the outside at the outside radius of the bend exceeds the ability of the cross-sectional shape and material properties of the malleable guide member (50) to support the stress.

Figure 9:
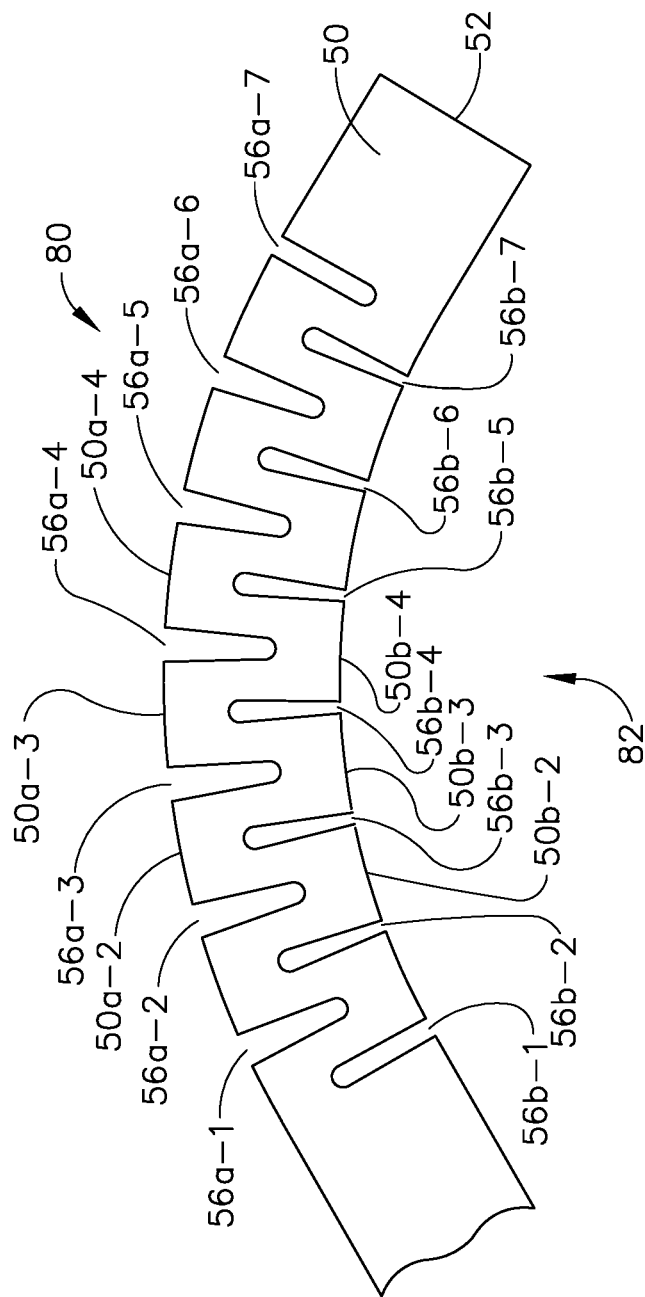
FIG. 9 depicts a side view of the malleable guide member of FIG. 7 with the guidewire omitted, with the malleable guide member in a bent configuration.

The exemplary malleable guide member (50) is configured with one or more stress limiting features which function to prevent the stress in malleable guide member (50), such as at the outside and/or inside radius of the bend, from exceeding such stress limit of the cross-sectional shape during bending so as to maintain the integrity of the initial cross-sectional shape sufficiently enough to avoid unacceptable trackability with guidewire (60) and dilation catheter (70) and unacceptable resistance to movement of guidewire (60). As seen in FIGS. 7-9, malleable guide member (50) includes a plurality of stress limiting features (56). Stress limiting features (56) may have any suitable configuration and location which function to limit stress in malleable guide member (50) during the bending process.

In FIGS. 7-9, stress limiting features (56) are configured as notches (56a), (56b) in malleable guide member (50) which form discrete voids in malleable guide member (50). Notches (56a), (56b) may be formed by any suitable means, such as by being laser cut. Notches (56a) are spaced apart and disposed on the same side of the cylindrically shaped malleable guide member (50). Each notch end is rounded, configured to minimize stress at the notch end during bending of malleable guide member (50). Notches (56a) are illustrated as subtending, circumferentially, an angle of greater than 180°, locating the notch ends below the horizontal mid line (as illustrated in FIGS. 7 & 8). In FIGS. 7-9, notches (56b) are disposed 180° opposite notches (56a), but are otherwise configured the same. Notches (56b) are illustrated as disposed equidistant between pairs of adjacent notches (56a). The number of notches (56a) and notches (56b) may be the same, thus leaving a notch (56a), (56b) at either end which is not in-between a pair of adjacent notches on the other side of malleable guide member (50).

Although notches (56a), (56b) are symmetrical to each other, offset axially, it is noted that symmetry of the notches and each notch's characteristics (e.g., orientation, spacing, size, etc.) is not required. Malleable guide member (50) may be configured with notches (56a) only on one side. The inter-notch spacing 58 between each notch (56a), (56b) on a respective side may be constant or may vary. The width of each notch (56a), (56b) in the axial direction may be constant or vary. The angle subtended by each notch (56a), (56b) may be constant or vary. The angular orientation (when viewed axially) of each notch (56a), (56b) may be constant or may vary. The angular orientation (when viewed radially) of each notch (56a),(56b) (illustrated as 90° relative to the axis of malleable guide member (50)) may be constant or vary. Such aforementioned attributes and configurations may be as are suitable.

FIG. 9 illustrates malleable guide member (50) bent to a selected shape. Bend (80) may have a single center (82) or multiple centers, and may be bent at a single radius throughout bend (80) or bend (80) may have multiple radii. Notches (56*a*) are disposed at the outside of bend (80), with notches (56*b*) disposed at the inside of bend (80). The voids at the outside of bend (80) formed by notches (56*a*) function to limit the stress at the outside of bend (80) that can result from the bending process. Notches (56*a*) separate the surface of malleable guide member (50) into discrete spaced apart sections (50*a*). As illustrated in FIG. 9, the axial widths of some notches (56*a*) at the outer diameter of bend (80) have increased and the sides of some notches (56*a*) are no longer parallel. The axial widths may vary from notch to notch, depending on the configuration of bend (80) as well as the way in which bend (80) was formed. Notch (56*a*-7) is illustrated as unchanged as that area of malleable guide member (50) is illustrated as not bent. The change in the axial width of notches (56*a*) at the outer diameter resulting from a bending process depends on the specific configuration of the specific notch (56*a*).

With the presence of stress limiting features 56 as malleable guide member (50) is bent, stress at the outer surface of bend (80) of one section, such as section (50*a*-3), is not transmitted to either adjacent section (50*a*-2), (50*a*-4) at the outer surface. The discontinuities of material at the outer diameter of bend (80) reduces the plastic deformation of malleable guide member (80) at the outer diameter of bend (80), reducing the stress and allowing malleable guide member (80) to substantially maintain its initial internal and external cross-sectional shape throughout bend (80).

As illustrated in FIG. 9, the axial widths of some notches (56*b*) at the inside of bend (80) have reduced and the sides of notches (56*b*) are no longer parallel, converging at the inside of bend (80). Stress at the inside of bend (80) is limited due to the voids of notches (56*b*). Stress at the inner surface of one section, such as section (50*b*-3) is not transmitted to either adjacent section (50*b*-2), (50*b*-4) at the inner surface.

The locations of stress limiting features (56) illustrated in FIGS. 7-9, disposed along opposite sides of malleable guide member (50) function to reduce stress for bi-directional bending, such as bending in the same or opposite direction illustrated in FIG. 9. Although stress limiting features (56) are illustrated on opposite sides, adequate resistance to ovalization may be achieved with stress limiting features (56) on only one side of malleable guide member (50), such as the outside of a bend.

Stress limiting features (56) may be configured to function for multi-directional bending. For example, the angular orientation of notches (56*a*), (56*b*) could change from notch to notch, creating an axial pattern of the angular orientations progressing along the axis of malleable guide member (50).

Although stress relieving features (56) are illustrated as voids resulting from notches (56*a*), (56*b*), stress relieving features may be of any suitable shape, orientation and location which function to maintain the integrity of the initial internal and external cross-sectional shape during the bending process. For example, stress relieving features (56) may be reductions in wall thickness at suitable locations, possibly configured similar to notches (56*a*), (56*b*) without forming a void. Such reduced wall thickness areas at the outside of a bend could be frangible and separate during the bending process.

Additionally, malleable guide member (50) may be annealed in one or more localized region, thereby decreasing the force required to bend malleable guide member (50) at such localized region(s). Such annealing may be localized axially as well as circumferentially (e.g., a circumferential segment may be annealed for less than 360°). Such localized regions of annealing may function as stress limiting features, as well as to cause certain areas of malleable guide member (50) to bend before or more than non-annealed regions.

III. Exemplary Bending Apparatus

FIGS. 10-17 show an exemplary bending apparatus (100) that may be used to bend malleable guide member (50) and maintain its external cross-sectional shape, thereby maintaining its internal cross-sectional shape, whether or not malleable guide member (50) is configured with stress reducing features. Bending apparatus (100) includes ram die (110) and pressure die (120). Bending apparatus (100) may be mounted to any suitable device for operation, such as a press or a plier. Ram die (110) is rigid and defines the radius or radii of the bend which is formed in the malleable guide member (50). Ram die (110) of exemplary bending apparatus (100) is configured to establish a cross-sectional profile restraint for that portion of the malleable guide member (50) which forms the inside of the bend, thereby maintaining, in cooperation with pressure die (120), the external cross-sectional shape of malleable guide member (50) during the bending process. Ram die (110) defines bend channel (112) which has a cross-sectional profile along the length of bend channel (112) that is complementarily shaped to malleable guide member (50). Bend channel (112) has a cross-sectional profile that conforms closely to half of the outer perimeter of malleable guide member (50). In exemplary bending apparatus (100), bend channel (112) has a cross-sectional profile is shaped as half a circle exactly matching 180° of the circumference (also referred to as the outside diameter (OD)) of malleable guide member (50). Bend channel (112) may have any suitable cross-sectional profile that adequately supports the portion of the outside diameter of malleable guide member (50) during bending, in cooperation with pressure die (120). The other shape of bend channel (112), the bend shape which is viewed from the side of ram die (110), may also be any suitable shape. The bend shape may be circular, may have a constant radius; may be elliptical; may be a complex curve; may have multiple radii; and/or may have multiple centers of curvature. Bend channel (112) may have any shape suitable for the forming the desired bend or bends in malleable guide member (50).

Figure 10:
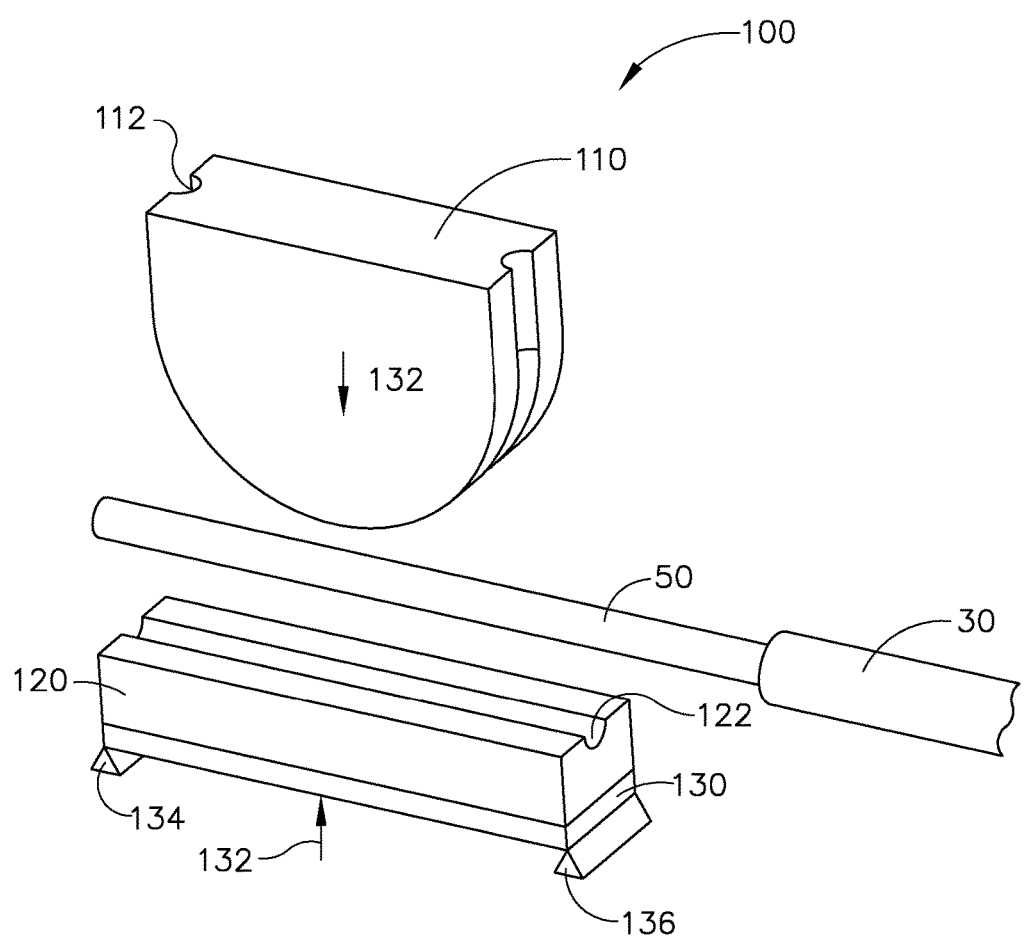
FIG. 10 depicts a perspective view of an exemplary bending instrument and a malleable guide member.

Pressure die (120) of exemplary bending apparatus (100) is configured to establish a cross-sectional profile restraint for that portion of the malleable guide member (50) which forms the outside of the bend, thereby maintaining, in cooperation with ram die (110) the external cross-sectional shape of malleable guide member (50) during the bending process. Pressure die (110) defines pressure channel (122) which extends linearly in a longitudinal direction as shown in an unloaded state as depicted in FIG. 10. During the bending process, ram die (110) and pressure die (120) are moved relative to each other in the direction of arrows (132), referred to herein as the press direction, which is generally perpendicular to the longitudinal direction. Pressure channel (122) is configured to receive malleable guide member (50), conforming closely to the outer perimeter of malleable guide member (112) that it receives. In exemplary bending apparatus (100), pressure channel (122) has a cross-sectional profile which is complementary to the shape of malleable guide member (50), shaped as a half circle similar to the cross-sectional profile of bend channel (112).

Pressure die (120) is sufficiently flexible in the press direction (132), transverse to the longitudinal direction, along the length of pressure channel (122) so as to bend in conformation to the bend shape of ram die (110) when pressure die (120) and ram die (110) are urged toward each other during bending of malleable guide member (50), as described below. Pressure die (120) is sufficiently stiff in the radial directions of pressure channel (122) to provide support to the outside diameter of the portion of malleable guide member (50) contacted by pressure channel (122) sufficient to substantially maintain, in cooperation with pressure die (120), the internal and external shape of malleable guide member (50) during the bending process. Pressure die (120) may be made of any suitable material.

Support (130) resiliently supports pressure die (120), which may be secured thereto in any suitable manner as will be apparent to those of ordinary skill in the art in view of the teachings herein. Support (130) is flexible in the press direction (132). Support (130) is supported at or adjacent its respective ends by supports (134), (136) which are illustrated diagrammatically. Supports (134), (136) allow the ends of support (130) to rotate and translate as necessitated by the deflection of support (130) resulting from conformation of pressure die (120) to ram die (110) during bending of malleable guide member (50).

As depicted in FIGS. 10, 11A and 11B, malleable guide member (50) is disposed overlying pressure channel (122) at a location that corresponds to the bend that is to be formed in malleable guide member (50). In FIG. 11B the complementary and close conformity of the shapes of bend channel (112) and pressure channel (122) to malleable guide member (50) can be seen.

FIGS. 12A and B illustrate the first step in bending malleable guide member (50), placing malleable guide member (50) into pressure channel (122). Thereafter, as depicted in FIGS. 13A and 13B, ram die (110) moves relative to pressure die (120) to contact and be urged against pressure die (120). Malleable guide member (50) is encircled by bend channel (112) and pressure channel (122) at the apex (110a), which is the point of first contact between bend channel (112) and malleable guide member (50). FIG. 13C illustrates radially inward forces about the circumference of malleable guide member (50) exerted by bend channel (112) and pressure channel (122) on malleable guide member (50) at line 13B-13B of FIG. 13A. These forces are sufficient to maintain the initial internal and external cross-sectional shape of malleable guide member (50) throughout the bending procedure. In FIGS. 13A-13C, the forces are present at the apex (110a) and adjacent regions to the extent that bend channel (112) and pressure channel (120) encircle malleable guide member (50). These forces may be present as a result of the relative position and force between ram die (110) and pressure die (120) and as a result of how closely bend channel (112) and pressure channel (122) conform to malleable guide member (50), and/or may comprise reaction forces exerted by bend channel (112) and pressure channel (122) in response to forces exerted by malleable guide member (50) resulting from stresses developed due to bending which would cause ovalization of malleable guide member (50) if bend channel (112) and pressure channel (122) were not both present.

As ram die (110) and pressure die (120) are urged toward each other in the press direction (132), ram die (110) extends into pressure die (120) as pressure die (120) conforms thereto, causing malleable guide member (50) to bend or wrap around ram die (110) matching the bend shape of ram die (110). As the conformity between ram die (110) and pressure die (120) progresses from apex (110a) to that illustrated in FIGS. 14A & 14B, with more of the arc length of pressure die (120) engaging ram die (110), bend channel (112), pressure (122) and the already encircled portion of malleable guide member (50) align and guide the adjacent non-encircled regions of malleable guide member (50) into bend channel (112).

Ram die (110) and pressure die (120) are configured to cooperate together to create two lines of tangency (114), (116) coincidental with malleable guide member (50) extending from tangent points (114a), (116a) located on bend channel (112) on either side of apex (110a). Tangent points (114a), (116a) are coincidental with each other when ram die (110) is disposed at apex (110a) and malleable guide member (50) is in its original straight form, and move away from each other around the bend shape during the bending operation as elastic deformation of pressure die (120) increases as ram die (110) advances into it, with pressure die (120) conforming to the bend shape of ram die (110). At all locations of malleable guide member (50) between the tangent points (114a), (116a), the cross-sectional shape of that portion of malleable guide member (50) is restrained by the cooperation of ram die (110) and pressure die (120) to maintain the external cross-sectional shape of malleable guide member (50).

Support (130) has deflected downwardly, providing the force that conforms pressure die (120) to ram die (110), providing the force of pressure channel (122) on malleable guide member (50) and from there to bend channel (112) to bend malleable guide member (50) about ram die (110) while maintaining its initial internal and external cross-sectional shape.

Figures 15A, 15B:
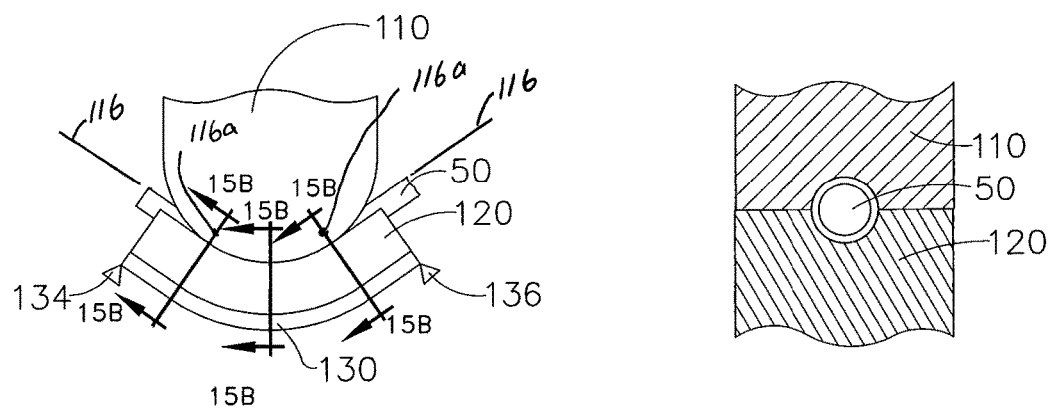
FIG. 15A depicts a side view of the exemplary bending instrument and malleable guide member of FIG. 10, with the bending instrument in a closed configuration and the malleable guide member in a fully bent configuration.
FIG. 15B depicts a cross-sectional view of the bending instrument and malleable guide member of FIG. 10, taken along 15B-15B of FIG. 15A.

FIGS. 15A & 15B illustrate the further progression of ram die (110) into pressure die (120) to its final position at which the bending of malleable guide member (50) is complete. As FIG. 15B depicts, the initial external and internal cross-sectional shape of malleable guide member (50) has been maintained throughout the bend. Tangent points (114a), (116a) have moved further apart along the length of malleable guide member (50) and the included angle between the two lines of tangency (114, (116) has decreased.

Figure 16:
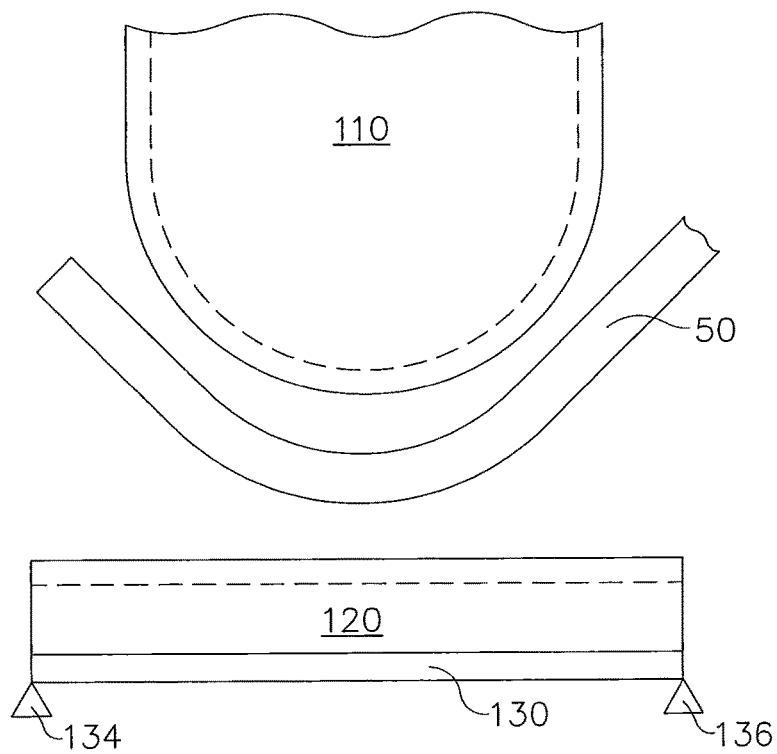
FIG. 16 depicts a side view of the exemplary bending instrument and malleable guide member of FIG. 10, with the bending instrument in an open configuration and the malleable guide member in a fully bent configuration.

In FIG. 16, ram die (110) has been retracted from pressure die (120), and malleable guide member (50) released, with pressure die (120) and support (130) returned to their unloaded configuration.

Figure 17:
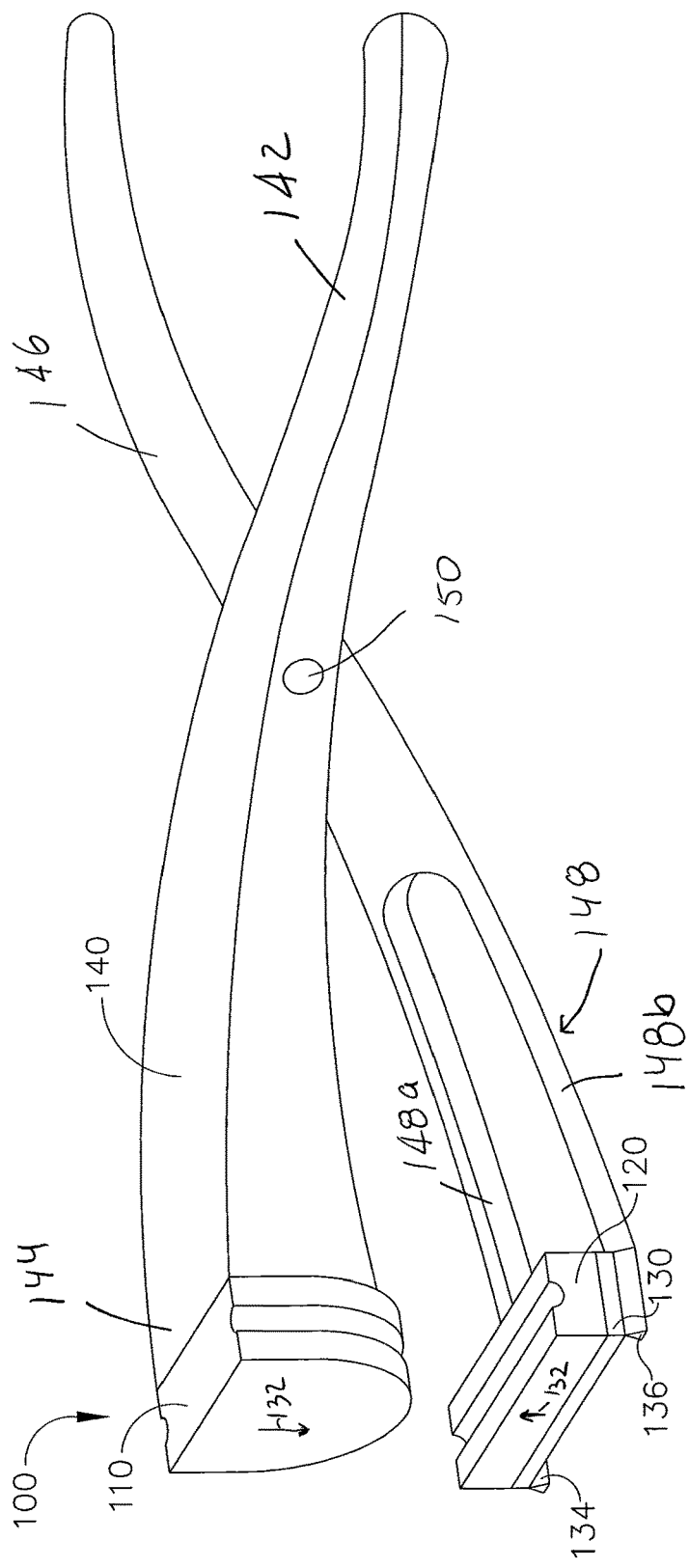
FIG. 17 depicts a perspective view of the exemplary bending instrument of FIG. 10 mounted to a plier type instrument.

As mentioned above, bending apparatus (100) may be mounted to any suitable device for operation, such as a press or a plier. The relative movement between ram die (110) and pressure die (120) and the force to urge the two against each other so as to bend malleable guide member (50) may be provided by any suitable power source, such as a hydraulic cylinder or ram operatively connected to either or both. FIG. 17 illustrates bending apparatus (100) mounted to pliers (140) where the power source may be a hand, or any other suitable source which may be coupled to pliers (140). Pliers (140) includes first handle (142) with first jaw (144) and second handle (146) with second jaw (148). First handle (142) and second handle (146) are pivotable relative to each other about joint (150). Ram die (110) is mounted to the distal end of first jaw (144) and pressure die (120) is mounted to the distal end of second jaw (148). Second jaw (148) may be configured as two spaced apart member (148a), (148b) to which supports (134), (136) are respectively mounted. Moving first handle (142) and second handle (146) together move ram die (110) and pressure die (120) toward each other in the press direction (132). Force applied to the proximal ends of the first and second handles (142), (146) urges ram die (110) and pressure die (120) against each other so as to bend malleable guide member (50) disposed in bend channel (112) and pressure channel (122).

IV. Exemplary Bending Fixture

Figure 18:
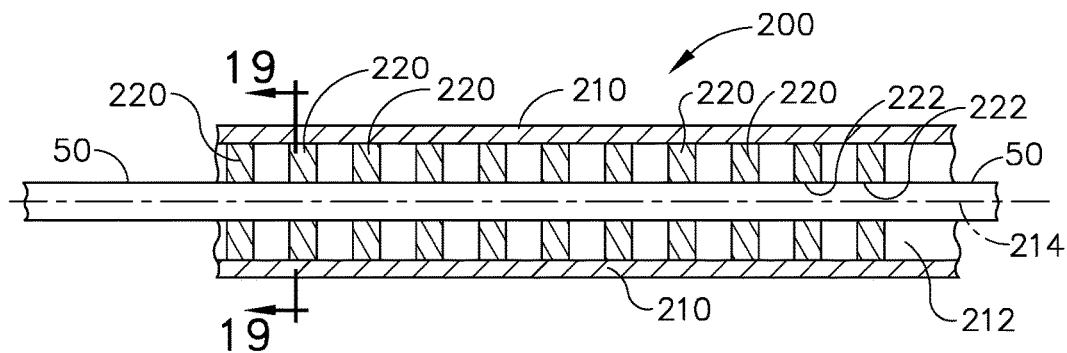
FIG. 18 is a longitudinal cross-sectional view of an exemplary bending fixture.
Figure 19:
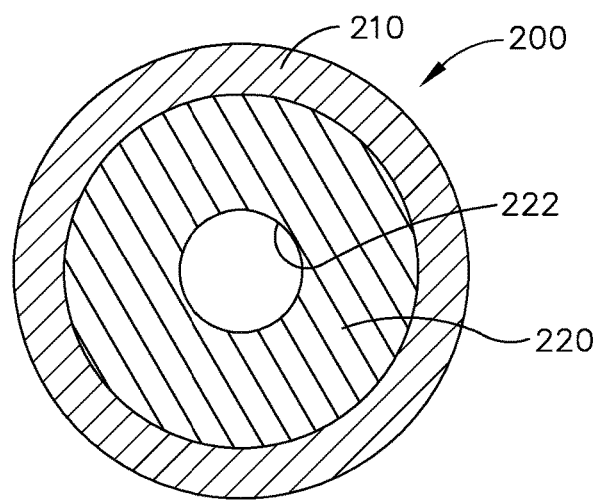
FIG. 19 depicts a cross-sectional view of the bending fixture of FIG. 18 taken along line 19-19 of FIG. 18 with the malleable guide member omitted for clarity.
Figure 20:
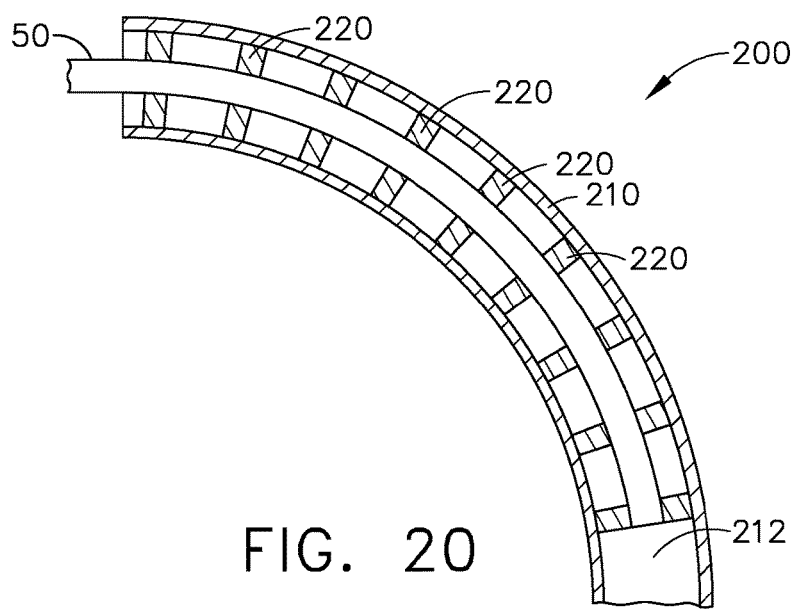
FIG. 20 depicts a longitudinal cross-sectional view of the bending fixture of FIG. 18 in a bent configuration.

FIGS. 18-20 show an exemplary bending fixture (200) that may be used to support malleable guide member (50) during bending to maintain its initial internal and external cross-sectional shape, whether or not malleable guide member (50) is configured with stress reducing features. Bending fixture (200) includes flexible tube (210) and a plurality of supports (220) disposed within the internal lumen (212) of flexible tube (210). Supports (220) may be spaced apart as illustrated, or may be immediately adjacent one another. Supports (220) may be equally spaced as illustrated, or may be unequally spaced. Supports (220) may be made of any suitable material sufficient to maintain the initial internal and external cross-sectional shape of malleable guide member (50), such as plated brass, stainless steel, plated carbon steel, ceramic, sintered metal or made via metal injection molded process. Spacers may be disposed in-between supports (220) to locate and maintain the spacing therebetween.

Each support (220) is connected to tube (210) to maintain its position within flexible tube (210), and may be secured thereto by any suitable means, such as adhesively bonded to flexible tube (210). Each support (220) a centrally disposed opening (222) generally aligned with longitudinal central axis (214) of flexible tube (210). Openings (222) are complementary in size and shape to the outside diameter of malleable guide member (50) such that when malleable guide member (50) is disposed through the openings (222) of the plurality of supports (220), openings (222) fully encircle and engage the outer diameter of malleable guide member (50).

Flexible tube (210) may undergo any bending process, whether done by hand or put in a bending apparatus and bent thereby. As flexible tube (210) goes through the bending process, supports (220) act on malleable guide member (50) to bend it. The conformity of openings (222) of supports (220) to malleable guide member (50) maintains the initial internal and external cross-sectional shape of malleable guide members (50).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a ram die comprising a bend channel, wherein the bend channel is configured to engage a portion of a guide member of an instrument configured to access a paranasal sinus, the portion having a cross-sectional shape, wherein the bend channel defines a bend shape; (b) a pressure die comprising a pressure channel, wherein the pressure channel is configured to engage a portion of the guide member; (c) wherein the ram die and the pressure die are configured to be moved toward and urged against each other in a press direction during a bending operation, wherein the ram die and the pressure die are configured to cooperate together to maintain the cross-sectional shape during the bending operation.

Example 2

The apparatus of Example 1, wherein the cross-sectional shape is an internal cross-sectional shape.

Example 3

The apparatus of any one or more of Examples 1 through 2, wherein the ram die and the pressure die are configured to cooperate together to create first and second lines of tangency during the bending operation, and wherein the first and second lines of tangency which are coincidental with the guide member.

Example 4

The apparatus of Example 3, wherein the first line of tangency extends from a first tangent point located on the bend channel on a first side of an apex of the ram die and the second line of tangency extends from a second tangent point located on the bend channel on a second side of the apex, the second side being opposite of the first side.

Example 5

The apparatus of Example 4, wherein the bend channel and the pressure channel encircle the guide member portion which is disposed between the first and second tangent points.

Example 6

The apparatus of any one or more of Examples 4 through 5, wherein the ram die and the pressure die are configured such that first tangent point and the second tangent point move away from each other around the bend shape as deformation of the pressure die increases the ram die advances into the deforming pressure die and the bending operation progresses.

Example 7

The apparatus of any one or more of Examples 1 through 6, wherein the pressure die is configured to elastically deform when the ram die advances into the pressure die during the bending operation.

Example 8

The apparatus of Example 7, wherein the pressure die is configured to conform to the bend shape when the ram die advances into the pressure die.

Example 9

The apparatus of any one or more of Examples 1 through 8, wherein the bend channel comprises a cross-sectional profile shaped complementarily to the cross-sectional shape.

Example 10

The apparatus of Example 9, wherein the pressure channel comprises a cross-sectional profile shaped complementarily to the cross-sectional shape, and wherein the bend channel cross-sectional profile and the pressure channel cross-sectional profile cooperate to encircle sections of the guide member while the sections are undergoing bending and to exert a force on the sections sufficient to maintain the cross sectional shape of such sections.

Example 11

The apparatus of any one or more of Examples 1 through 10, wherein the bend channel comprises a cross-sectional profile and the pressure channel comprises a cross-sectional profile which cooperate to encircle the portion of the guide member.

Example 12

The apparatus of Example 11, wherein the cross-sectional shape is circular, wherein the bend channel cross-sectional profile is a half circle, and wherein the pressure channel cross-sectional profile is a half circle.

Example 13

The apparatus of any one or more of Examples 1 through 12, wherein the pressure channel extends in a longitudinal direction when the pressure die is in an unloaded state, and wherein the longitudinal direction is transverse to the press direction.

Example 14

The apparatus of Example 13, wherein the pressure channel is sufficiently stiff in radial directions relative to the longitudinal direction to provide support to the cross-sectional shape sufficient to maintain the cross-sectional shape during the bending operation.

Example 15

The apparatus of any one or more of Examples 1 through 14, comprising a pliers, wherein the pliers comprises a first jaw and a second jaw which are movable toward each other, wherein the ram die is mounted to the first jaw and the pressure die is mounted to the second jaw.

Example 16

An apparatus comprising: (a) a ram die comprising a bend channel, wherein the bend channel is configured to engage a portion of a guide member of an instrument configured to access a paranasal sinus, the portion having a cross-sectional shape, wherein the bend channel defines a bend shape; (b) a pressure die comprising a pressure channel, wherein the pressure channel is configured to engage a portion of the guide member; (c) wherein the ram die and the pressure die are configured to be moved toward and urged against each other in a press direction during a bending operation, wherein the pressure die is configured to conform to the bend shape when the ram die advances into the pressure die.

Example 17

The apparatus of Example 16, wherein the pressure channel extends in a longitudinal direction when the pressure die is in an unloaded state, wherein the longitudinal direction is transverse to the press direction, and wherein the pressure channel is sufficiently stiff in radial directions relative to the longitudinal direction to provide support to the cross-sectional shape sufficient to maintain the cross-sectional shape during the bending operation.

Example 18

The apparatus of any one or more of Examples 16 through 17, wherein the bend channel comprises a cross-sectional profile and the pressure channel comprises a cross-sectional profile which cooperate to encircle the portion of the guide member.

Example 19

The apparatus of any one or more of Examples 16 through 18, wherein the ram die and the pressure die are configured to cooperate together during the bending operation to create a first line of tangency extending from a first tangent point located on the bend channel on a first side of an apex of the ram die and to create a second line of tangency extending from a second tangent point located on the bend channel on a second opposite side of the apex, and wherein the bend channel and the pressure channel encircle the guide member portion which is disposed between the first and second tangent points.

Example 20

An apparatus comprising: (a) a ram die comprising a bend channel, wherein the bend channel is configured to engage a portion of a guide member of an instrument configured to access a paranasal sinus, the portion having a cross-sectional shape, wherein the bend channel defines a bend shape, wherein the bend channel comprises a cross-sectional profile shaped complementarily to the cross-sectional shape; (b) a pressure die comprising a pressure channel, wherein the pressure channel extends linearly in a longitudinal direction when unloaded, wherein the pressure die is configured to engage the portion of the guide member, wherein the pressure channel comprises a cross-sectional profile shaped complementarily to the cross-sectional shape; (c) wherein the ram die and the pressure die are configured to be moved relative to each other in a press direction during a bending operation, wherein the bend channel cross-sectional profile and the pressure channel cross-sectional profile cooperate together to fully encircle the portion of the guide member at two spaced apart points of tangency and all points therebetween during the bending operation.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) a ram die including a bend channel, wherein the bend channel defines a first surface shaped to engage a portion of a guide member of an instrument configured to access a paranasal sinus, the portion having a cross-sectional shape, wherein the bend channel defines a bend shape; and
(b) a pressure die including a pressure channel, wherein the pressure channel defines a second surface shaped to engage the portion of the guide member;
wherein the ram die and the pressure die are configured to be moved toward and urged against each other in a press direction during a bending operation, wherein the first surface of the ram die and the second surface of the pressure die are configured to cooperate together to maintain the cross-sectional shape during the bending operation; and
wherein the pressure die includes an elastically deformable material configured to deform when the ram die advances into the pressure die during the bending operation.

2. The apparatus of claim 1, wherein the cross-sectional shape is an internal cross-sectional shape.

3. The apparatus of claim 1, wherein the ram die and the pressure die are configured to cooperate together during the bending operation to create first and second lines of tangency, and wherein the first and second lines of tangency which are coincidental with the guide member.

4. The apparatus of claim 3, wherein the first line of tangency extends from a first tangent point located on the bend channel on a first side of an apex of the ram die and the second line of tangency extends from a second tangent point located on the bend channel on a second side of the apex, the second side being opposite of the first side.

5. The apparatus of claim 4, wherein the bend channel and the pressure channel encircle the guide member portion which is disposed between the first and second tangent points.

6. The apparatus of claim 4, wherein the ram die and the pressure die are configured such that first tangent point and the second tangent point move away from each other around the bend shape as deformation of the pressure die increases the ram die advances into the deforming pressure die and the bending operation progresses.

7. The apparatus of claim 1, wherein the pressure die is configured to conform to the bend shape when the ram die advances into the pressure die.

8. The apparatus of claim 1, wherein the bend channel defines a cross-sectional profile shaped complementarily to the cross-sectional shape.

9. The apparatus of claim 8, wherein the pressure channel defines a cross-sectional profile shaped complementarily to the cross-sectional shape, and wherein the bend channel cross-sectional profile and the pressure channel cross-sectional profile cooperate to encircle sections of the guide member while the sections are undergoing bending and to exert a force on the sections sufficient to maintain the cross sectional shape of such sections.

10. The apparatus of claim 1, wherein the bend channel defines a cross-sectional profile and the pressure channel defines a cross-sectional profile which cooperate to encircle the portion of the guide member.

11. The apparatus of claim 10, wherein the cross-sectional shape is circular, wherein the bend channel cross-sectional profile is a half circle, and wherein the pressure channel cross-sectional profile is a half circle.

12. The apparatus of claim 1, wherein the pressure channel extends in a longitudinal direction when the pressure die is in an unloaded state, and wherein the longitudinal direction is transverse to the press direction.

13. The apparatus of claim 12, wherein the pressure channel is sufficiently stiff in radial directions relative to the longitudinal direction to provide support to the cross-sectional shape sufficient to maintain the cross-sectional shape during the bending operation.

14. The apparatus of claim 1, comprising a pliers, wherein the pliers includes a first jaw and a second jaw which are movable toward each other, wherein the ram die is mounted to the first jaw and the pressure die is mounted to the second jaw.

15. An apparatus, comprising:
(a) a ram die including a bend channel, wherein the bend channel defines a first surface shaped to engage a portion of a guide member of an instrument configured to access a paranasal sinus, the portion having a cross-sectional shape, wherein the bend channel defines a bend shape; and
(b) a pressure die including a pressure channel, wherein the pressure channel defines a second surface shaped to engage the portion of the guide member;
wherein the ram die and the pressure die are configured to be moved toward and urged against each other in a press direction during a bending operation, wherein the pressure die is configured to deform to thereby conform to the bend shape when the ram die advances toward and applies pressure to the pressure die.

16. The apparatus of claim 15, wherein the pressure channel extends in a longitudinal direction when the pressure die is in an unloaded state, wherein the longitudinal direction is transverse to the press direction, and wherein the pressure channel is sufficiently stiff in radial directions relative to the longitudinal direction to provide support to the cross-sectional shape sufficient to maintain the cross-sectional shape during the bending operation.

17. The apparatus of claim 15, wherein the bend channel comprises a cross-sectional profile and the pressure channel comprises a cross-sectional profile which cooperate to encircle the portion of the guide member.

18. The apparatus of claim 15, wherein the ram die and the pressure die are complementarily shaped to cooperate together during the bending operation to create a first line of tangency extending from a first tangent point located on the bend channel on a first side of an apex of the ram die and to create a second line of tangency extending from a second tangent point located on the bend channel on a second opposite side of the apex, and wherein the bend channel and the pressure channel encircle the guide member portion which is disposed between the first and second tangent points.

19. An apparatus comprising:
(a) a ram die including a bend channel, wherein the bend channel defines a first surface shaped to engage a portion of a guide member of an instrument configured to access a paranasal sinus, the portion having a cross-sectional shape, wherein the bend channel defines a bend shape, wherein the first surface defines a cross-sectional profile shaped complementarily to the cross-sectional shape; and
(b) a pressure die comprising a pressure channel, wherein the pressure channel extends linearly in a longitudinal direction when unloaded, wherein the pressure die defines a second surface shaped to engage the portion of the guide member, wherein the second surface defines a cross-sectional profile shaped complementarily to the cross-sectional shape; and
wherein the ram die and the pressure die are configured to be moved relative to each other in a press direction during a bending operation, wherein the bend channel cross-sectional profile and the pressure channel cross-sectional profile cooperate together to fully encircle the portion of the guide member at two spaced apart points of tangency and all points therebetween during the bending operation; and
wherein the pressure die includes an elastically deformable material configured to deform when the ram die and the pressure die move relative to each other during the bending operation.

20. The apparatus of claim 15, comprising a pliers, wherein the pliers includes a first jaw and a second jaw which are movable toward each other, wherein the ram die is mounted to the first jaw and the pressure die is mounted to the second jaw.

* * * * *